United States Patent [19]

Muraoka

[11] Patent Number: 5,589,162
[45] Date of Patent: Dec. 31, 1996

[54] HAIR SETTING AGENT COMPOSITION

[75] Inventor: Tsutomu Muraoka, Tokyo, Japan

[73] Assignee: Kao Corporation, Tokyo, Japan

[21] Appl. No.: 425,062

[22] Filed: Apr. 19, 1995

[30] Foreign Application Priority Data

Apr. 28, 1994 [JP] Japan ................................. 6-091315

[51] Int. Cl.⁶ .............................. A61K 7/11; A61K 7/06
[52] U.S. Cl. ................. 424/70.12; 424/70.122; 424/70.11; 424/DIG. 2; 424/47
[58] Field of Search ................ 424/70.11, 70.12, 424/70.122

[56] References Cited

U.S. PATENT DOCUMENTS

| | | | |
|---|---|---|---|
| 4,150,216 | 4/1979 | Quack et al. | 528/290 |
| 4,151,269 | 4/1979 | Torii et al. | 424/47 |
| 4,300,580 | 11/1981 | O'Neill et al. | 132/7 |
| 4,910,013 | 3/1990 | Kanamaru et al. | 424/47 |
| 5,158,762 | 10/1992 | Pierce . | |

FOREIGN PATENT DOCUMENTS

| | | |
|---|---|---|
| 2074293 | 1/1993 | Canada . |
| 0285364 | 10/1988 | European Pat. Off. . |
| 0524346 | 1/1993 | European Pat. Off. . |
| 0551749 | 7/1993 | European Pat. Off. . |

OTHER PUBLICATIONS

Database WPI. Week 9121. Derwent Publications Ltd., London, GB; AN 91–151080. XP002006250 & JP–A–02 172 905 (Mandum KK), 4 Jul. 1990. *abstract*.

Database WPI. Week 9416. Derwent Publications Ltd., London, GB; AN 94–131952. XP002006251 & JP–A–06 080 538 (Kao Corp.), 22 Mar. 1994. *abstract*.

*Primary Examiner*—Sallie M. Gardner
*Attorney, Agent, or Firm*—Oblon, Spivak, McClelland, Maier & Neustadt, P.C.

[57] ABSTRACT

A hair setting agent composition is disclosed, which comprises: (A) 0.01 to 10% by weight of a water-dispersible polyester resin; (B) 0.01 to 10% by weight of at least one silicone derivative; and (C) 0.1 to 40% by weight of a $C_{8-40}$ hydrocarbon oil. The hair setting agent composition according to the present invention exhibits excellent hair setting properties and set retaining properties and provides hairs with a nonsticky smooth finish touch and a natural gloss.

6 Claims, No Drawings

HAIR SETTING AGENT COMPOSITION

FIELD OF THE INVENTION

The present invention relates to a hair setting agent composition. More particularly, the present invention relates to a hair setting agent composition which has excellent setting properties and set retaining properties and which provides hairs with a nonsticky smooth finish touch and a natural gloss.

BACKGROUND OF THE INVENTION

In general, hair setting agents such as a hair foam, a hair spray, a setting lotion and a hair gel incorporate a film-forming resin for the purpose of providing a hair setting capacity and a set retaining capacity. Further, the hair setting agent comprises a silicone oil for the purpose of improving the finish touch.

However, the film-forming resin which has heretofore been incorporated in hair setting agents is disadvantageous in that the resulting set hair can easily get out of shape under a high humid atmosphere or in a violent motion, though it has some setting capacity in normal use. In particular, a hair setting agent comprising a silicone oil, an ester oil, a hydrocarbon oil or the like provides an improved finish touch but gives a set hair which can get out of shape more easily and thus exhibits a remarkably reduced set retaining properties.

SUMMARY OF THE INVENTION

It is therefore an object of the present invention to provide a hair setting agent composition which has excellent setting properties and set retaining properties and which provides a smooth finish touch and a natural gloss.

Under these circumstances, the inventor made extensive studies. As a result, it was found that the combined use of a water-dispersible polyester resin and a silicone derivative results in a hair setting agent composition which has excellent setting properties and set retaining properties and which provides a nonsticky smooth finish touch and a natural gloss.

Namely, the present invention provides a hair setting agent composition comprising:

(A) 0.01 to 10% by weight of a water-dispersible polyester resin;

(B) 0.01 to 10% by weight of at least one silicone derivative selected from the group consisting of a polyether-modified silicone, a dimethyl polysiloxane, a methylphenyl polysiloxane, a diphenyl polysiloxane, a long-chain alkyl-modified silicone, an alkoxy-modified silicone, an amino-modified silicone, a Bunte salt-modified silicone and a silicone resin; and (C) 0.1 to 40% by weight of a $C_{8-40}$ hydrocarbon oil.

DETAILED DESCRIPTION OF THE INVENTION

The water-dispersible polyester resin to be used as Component (A) in the present invention is not specifically limited so long as it is water-insoluble and water-dispersible. A preferred example of the water-dispersible polyester resin is a polyester having a —$SO_3M$ group (in which M represents a hydrogen atom or metal ion) in an amount sufficient to render the polyester dispersible in water, as disclosed in U.S. Pat. No. 4,335,220, herein incorporated by reference.

A preferred example of the polyester having —$SO_3M$ group includes one obtained by the condensation of at least one dicarboxylic acid, at least one diol and at least one bifunctional sulfo monomer having two functional groups and at least one sulfonic acid group on its aromatic nucleus.

As the dicarboxylic acid to be subjected to the condensation reaction there may be used any of aliphatic dicarboxylic acid, alicyclic dicarboxylic acid and aromatic dicarboxylic acid. Examples of these dicarboxylic acids include oxalic acid, malonic acid, dimethylmalonic acid, succinic acid, glutaric acid, adipic acid, trimethyladipic acid, pimelic acid, 2,2-dimethylglutaric acid, azelaic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, terephthalic acid, isophthalic acid, 2,5-norbornanedicarboxylic acid, 1,4-naphthal acid, diphenic acid, 4,4'-oxydibenzoic acid, diglycolic acid, thiodipropionic acid, 4,4'-sulfonyldibenzoic acid, 2,5-naphthalenedicarboxylic acid, and 2,6-naphthalenedicarboxylic acid. These dicarboxylic acids may be used singly or in combination of two or more of them.

Particularly preferred among these dicarboxylic acids are isophthalic acid, terephthalic acid, and phthalic acid.

Examples of the diol to be subjected to the condensation reaction include ethylene glycol, propylene glycol, 1,3-propanediol, 2,4-dimethyl-2-ethylhexane-1,3-diol, 2,2-dimethyl-1,3-propanediol, 2-ethyl-2-butyl-1,3-propanediol, 2-ethyl-2-isobutyl-1,3-propanediol, 1,3-butanediol, 1,4-butanediol, 1,5-pentanediol, 1,6-hexanediol, 2,2,4-trimethyl-1,6-hexanediol, thiodiethanol, 1,2-cyclohexanedimethanol, 1,3-cyclohexanedimethanol, 1,4-cyclohexanedimethanol, 2,2,4,4-tetramethyl-1,3-cyclobutanediol, p-xylylenediol, diethylene glycol, triethyelne glycol, tetraethylene glycol, pentaethylene glycol, hexaethylene glycol, heptaethylene glycol, octaethylene glycol, nonaethylene glycol, decaethylene glycol, hydroxypivalyl hydroxypivalate, dipropylene glycol, 1,10-decanediol, 1,3-butanediol, hydrogenated bisphenol A, 1,4-butanediol, and neopentyl glycol. These diols may be used singly or in combination of two or more of them.

Particularly preferred among these diols are diethylene glycol, cyclohexane dimethanol, triethylene glycol, ethylene glycol, 1,3-propanediol, and 1,4-butanediol.

Preferred examples of the bifunctional sulfo monomer having two functional groups and at least one sulfonic acid group on its aromatic nucleus (hereinafter referred to as "bifunctional sulfo monomer") include dicarboxylic acid having one or more —$SO_3M$ groups, derivatives thereof, and diol having one or more —$SO_3M$ groups. Examples of the metal ion represented by M in the —$SO_3M$ group include $Na^+$, $Li^+$, $K^+$, $Mg^{2+}$, $Ca^{2+}$, $Cu^{2+}$, $Fe^{2+}$ and $Fe^{3+}$. Particularly preferred among these metal ions are $Na^+$, $Li^+$, and $K^+$.

Examples of the aromatic nucleus to which the —$SO_3M$ group(s) is/are connected include benzene, naphthalene, anthracene, diphenyl, oxydiphenyl, sulfonyldiphenyl, and methylenediphenyl.

Preferred among these bifunctional sulfo monomers are sulfoisophthalic acid, sulfoterephthalic acid, sulfophthalic acid, 4-sulfonaphthalene-2,7-dicarboxylic acid, and derivatives or sodium salts thereof. Particularly preferred among these bifunctional sulfo monomers are sulfoisophthalic acid, and sulfoterephthalic acid.

These bifunctional sulfo monomers may be used singly or in combination of two or more of them.

The condensation reaction of the dicarboxylic acid, the diol and the bifunctional sulfo monomers can be effected in accordance with ordinary methods. For example, a mixture of these monomers may be heated to a temperature of about 200° C. in the presence of a catalyst such as dibutyltin oxide to obtain a water-dispersible polyester.

Particularly preferred among these water-dispersible polyesters is one obtained by the condensation of diethylene glycol, cyclohexane dimethanol, isophthalic acid and sulfoisophthalic acid. As the polyester there may be used a commercially available product such as Eastman AQ38S and 55S (available from Eastman Chemical Products Inc.).

These water-dispersible polyester resins may be used singly or in combination of two or more of them. The water-dispersible polyester resin may be incorporated in the composition in an amount of from 0.01 to 10% by weight, preferably from 0.1 to 8% by weight, more preferably from 1 to 6% by weight. If the content of the water-dispersible polyester falls below 0.01% by weight, the setting properties and set retaining properties tend to decrease. On the contrary, if the content of the water-dispersible polyester exceeds 10% by weight, it tends to give an impaired finish touch and a reduced gloss.

As the silicone derivative to be used as Component (B) there may be used one or more of compounds represented by the following formulae (a) to (g).
(a) Polyether-modified silicones represented by formulae (1) to (4):

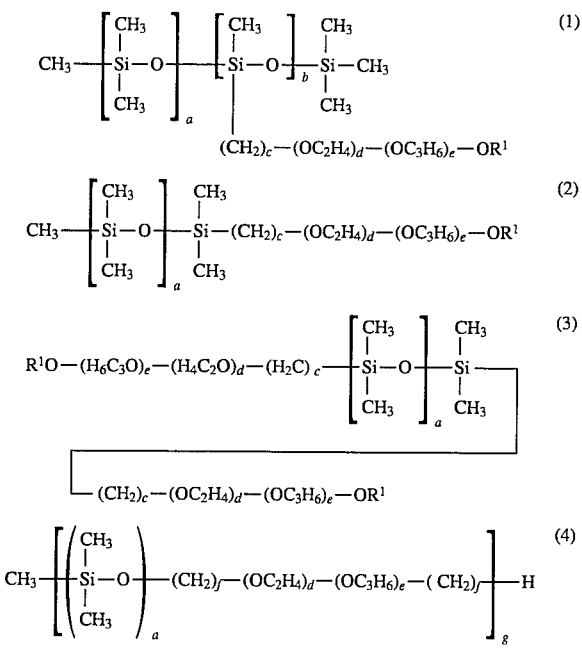

wherein $R^1$ represents hydrogen atom or a $C_{1-10}$ hydrocarbon group; a represents a number of 15 or more; b represents a number of 1 or more; c represents a number of 1 to 6; d represents a number of 1 to 300; e represents an number 0 to 300; f represents a number of 0 to 6; and g represents a number of 2 to 500.

The hydrocarbon group represented by $R^1$ is preferably a $C_{1-8}$ straight-chain or branched saturated hydrocarbon group, particularly methyl group. The number a is preferably from 20 to 500. The number b is preferably from 1 to 100. The number c is preferably from 2 to 4. The number d is preferably from 2 to 50. The number e is preferably from 0 to 50. The number f is preferably from 2 to 4. The number g is preferably from 2 to 50. If the number a falls below 15, an excellent finish touch is hardly obtained. As the polyether-modified silicone there may preferably be used a commercially available product. Preferred examples of the commercially available product include SH3772C, SH3773C, SH3775C (available from Toray Dow Corning Silicone Co., Ltd.), KF352A, KF353A, KF615A, KF945A (available from Shin-Etsu Chemical Co., Ltd.), Silwet L-7001, L-7002, L-7602 (available from Nihon Unicar Co., Ltd.).
(b) Dimethyl polysiloxane, methylphenyl polysiloxane or diphenyl polysiloxane represented by formula (5):

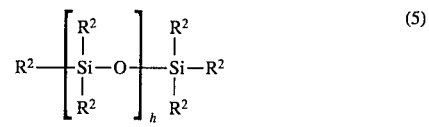

wherein $R^2$'S may be the same or different and each represent methyl group, phenyl group or $-OSi(CH_3)_3$; and h represents a number of 3 or more.

In formula (5), $R^2$ is preferably methyl group, and h is preferably from 50 to 3,000.

Particularly preferred among these polysiloxanes is dimethyl polysiloxane. For example, commercially available products such as SH200 Series (viscosity: not less than 100 cs), BY11-004 (available from Toray Dow Corning Silicone Co., Ltd.), KF96 Series (viscosity: not less than 100 cs), KF96H Series and X-21-7501G (available from Shin-Etsu Chemical Co., Ltd.) are preferred.
(c) Long-chain alkyl-modified silicone represented by formula (6):

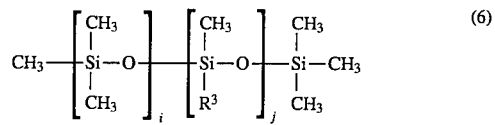

wherein $R^3$ represents a $C_{10-50}$ hydrocarbon group; i represents a number of 0 to 1,000; and j represents a number of 1 to 1,000.

In formula (6), the hydrocarbon group represented by $R^3$ is preferably a $C_{15-40}$ straight-chain or branched saturated hydrocarbon group, and i and j are each preferably from 10 to 500.
(d) Alkoxy-modified silicone represented by formula (7):

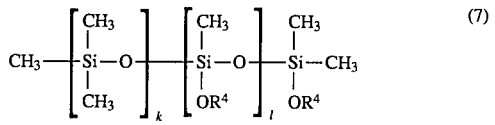

wherein $R^4$ represents a $C_{10-30}$ hydrocarbon group; k represents a number of 3 to 100; and l represents a number of 1 to 50.

The hydrocarbon group represented by $R^4$ is preferably a $C_{12-20}$ straight-chain or branched saturated hydrocarbon group, particularly cetyl group or stearyl group, k is preferably a number of 5 to 50, and l is preferably a number of 2 to 20.
(e) Amino-modified silicone represented by formula (8):

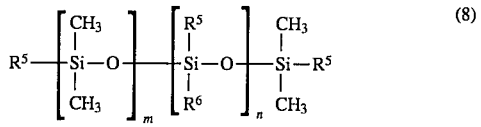

wherein $R^5$ may be the same or different and each represent hydrogen atom, hydroxyl group, methyl group or methoxy group; $R^6$ represents $-(CH_2)_o-$ $(OC_2H_4)_p-(OC_3H_6)_q-(NHC_2H_4)N(R^7)_2$ or —$(CH_2)_o$—$(OC_2H_4)_p$—$(OC_3H_6)_q$—$(NHC_2H_4)N^+$ $(R^7)_3.Z^-$ (in which $R^7$'s may be the same or different and each represents hydrogen atom or a $C_{1-6}$ hydrocarbon group; Z represents a halogen ion or an organic anion; o represents a number of 1 to 6; and p and q each represents a number of 0 to 6); m represents a number of 3 to 300; and n represents a number of 1 to 50.

In formula (8), $R^5$ is preferably hydroxyl group or methyl group, $R^6$ is preferably —$(CH_2)_3$—$NHC_2H_4NH_2$, m is preferably from 3 to 300, and n is preferably from 1 to 50.

(f) Bunte salt-modified silicone represented by formula (9) or (10):

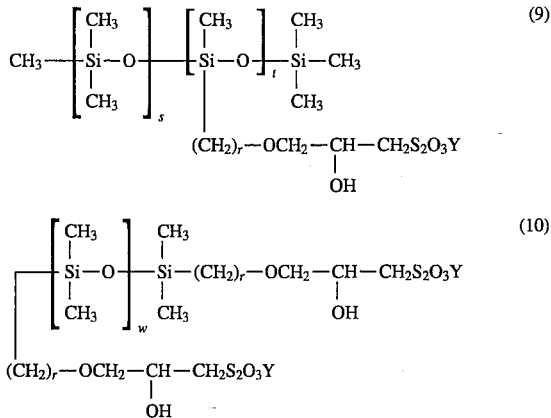

wherein Y represents an alkaline metal, ammonia, amine or quaternary ammonium salt; r represents a number of 1 to 6; and s and t each represents a number of 1 to 20, with the proviso that s and t satisfy the relationship s/t>1.

In formulae (9) and (10), Y is preferably an alkaline metal such as sodium and potassium or quaternary ammonium salt, r is preferably from 2 to 4, and s and t are each preferably from 5 to 20.

(g) Silicone resin represented by formula (11):

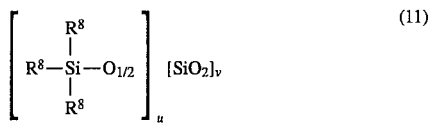

wherein $R^8$'s may be the same or different and each represent methyl group or phenyl group; and u and v each represent a number of 10 to 100, with the proviso that u and v satisfy the relationship u/v=0.1 to 10.

In formula (11), $R^8$ is preferably methyl group, and u and v are preferably from 10 to 50.

Particularly preferred among these silicone derivatives are polyether-modified silicone, dimethyl polysiloxane, methyl phenyl polysiloxane, and diphenyl polysiloxane.

These silicone derivatives may be used singly or in combination of two or more of them. The silicone derivative may be incorporated in the composition in an amount of from 0.01 to 10% by weight, preferably from 0.1 to 8% by weight, more preferably from 0.1 to 5% by weight. If the content of the silicone derivative in the composition falls below 0.01% by weight, a good touch is hardly obtained. On the contrary, if the content of the silicone derivative in the composition exceeds 10% by weight, it tends to give poor setting properties disadvantageously.

The mixing ratio of Component (A) and Component (B) by weight is preferably from 100/1 to 1/100, more preferably from 50/1 to 1/50.

In a particularly preferred embodiment of the present invention, a water-dispersible polyester resin obtained by the condensation of diethylene glycol, cyclohexane dimethanol, isophthalic acid and sulfoisophthalic acid may be used as Component (A). As Component (B) there may be used one or more selected from the group consisting of the polyether-modified silicone, the dimethyl polysiloxane, the methylphenyl polysiloxane and the diphenyl polysiloxane.

The $C_{8-40}$ hydrocarbon oil to be used as Component (C) is preferably a $C_{12-24}$ hydrocarbon oil, particularly $C_{12-16}$ branched saturated hydrocarbon oil. The blending of such a hydrocarbon oil advantageously provides hairs with a less sticky and smooth touch. If the number of carbon atoms contained in the hydrocarbon oil falls below 8, desirable effects are hardly exerted. On the contrary, if the number of carbon atoms contained in the hydrocarbon oil exceeds 40, the resulting set retaining properties tend to be impaired.

These hydrocarbon oils may be used singly or in combination of two or more of them. The hydrocarbon oil is preferably incorporated in the composition in an amount of from 0.1 to 40% by weight, more preferably from 0.5 to 30% by weight. In particular, when a hydrocarbon oil is incorporated in an amount of from 1 to 20% by weight, a better touch can be provided.

In addition to the foregoing components, the hair setting agent composition of the present invention may further comprise a surfactant. Any of anionic, nonionic, amphoteric and cationic surfactants can be used. Particularly preferred among these surfactants is a nonionic surfactant. Specific examples of such a nonionic surfactant include polyoxyalkylene-added alkyl ethers such as polyoxyethylene cetyl ether, polyoxyethylene stearyl ether, polyoxypropylene cetyl ether and polyoxyethylene oxypropylene cetyl ether.

The surfactant, if any, is preferably incorporated in the composition in an amount of from 0.01 to 5% by weight.

The hair setting agent composition of the present invention may furthermore comprise components which are commonly used as cosmetic materials in an amount that the effect of the present invention is not impaired. Examples of these components include glycerides such as castor oil, cocoa oil, avocado oil and olive oil; waxes such as beeswax, whale wax, lanolin and carnauba wax; alcohols such as cetyl alcohol, oleyl alcohol, hexadecyl alcohol, lauryl alcohol, stearyl alcohol, isostearyl alcohol, 2-octyldodecanol, propylene glycol, polypropylene glycol, glycerin and ethanol; esters such as isopropyl myristate, isopropyl laurate, hexyl laurate, cetyl lactate, propylene glycol monostearate, oleyl oleate, hexadecyl 2-ethylhexanoate and octyldodecyl myristate; polysaccharide thickening agents such as carrageenan, locust bean gum, hydroxyethyl cellulose and xanthane gum; parabenes such as methyl parabene and ethyl parabene; perfumes; dyes; antioxidant; ultraviolet absorbents; and vegetable extracts.

The preparation of the hair setting agent composition of the present invention can be prepared by ordinary methods. The hair setting agent composition of the present invention may be in the form of an aerosol or a nonaerosol. More specifically, the hair setting agent composition of the present invention may be in the form of a hair foam, a hair gel, a hair spray, a setting lotion, a hair cream and a pump mist.

If the hair setting agent composition of the present invention is formulated into the form of an aerosol, it may be contained in a pressure-resistant closed vessel together with a propellent. As the propellent there may be used a liquefied gas, a pressurized gas or the like. Specific examples of the propellent include dimethyl ether, liquefied petroleum gas, nitrogen gas, and carbon dioxide gas.

In the case where the hair setting agent composition of the present invention is formulated into the form of foam, preferred among these propellants are liquefied petroleum gas and dimethyl ether, and the propellent is preferably incorporated in the composition in an amount of from 3 to 50% by weight, more preferably from 5 to 25% by weight.

In the case where the hair setting agent composition of the present invention is formulated into a sprayable product with the use of a liquefied gas such as dimethyl ether and liquefied petroleum gas, the liquefied gas is preferably incorporated in the composition in an amount of from 10 to 70% by weight, more preferably from 20 to 60% by weight. On the other hand, where a pressurized gas such as nitrogen gas and carbon dioxide gas is used, it is preferably incorporated in the composition in an amount of from 0.01 to 5% by weight, more preferably from 0.1 to 3% by weight.

The hair setting agent composition of the present invention exhibits excellent setting properties and set retaining properties and can provide hair with a nonsticky smooth touch and a natural gloss.

The present invention will be further described hereinafter, but the present invention should not be construed as being limited thereto.

EXAMPLE 1

A foamable hair setting agent having the formulation set forth in Table 1 was prepared in an ordinary method.

The setting agent thus obtained was then evaluated for its set retaining properties and nonstickiness, smooth touch and gloss after finish. The results are set forth in Table 1.
(Evaluation Method)
(1) Set retention:

A bundle of hairs having a length of 18 cm and a weight of 1.5 g was washed with a standard shampoo, and the dampness was then wiped off with a towel. The hair bundle was coated with 0.2 g of the hair setting agent, and then wound on a 2-cm diameter rod, followed by spontaneous drying. The hair bundle thus dried was removed from the rod and then mounted onto a shaker. The hair bundle was then shaken at a temperature of 20° C. and 98% RH at a frequency of 120 cycles per minute for 30 minutes. The elongation of the curl was then observed to determine the set retaining properties according to the following equation:

Set retaining properties = $(L-L_1)/(L-L_0) \times 100$ where

L: Initial length of the hair bundle (18 cm);

$L_0$: Length of the hair bundle immediately after the removal from the rod; and $L_1$: Length of the hair bundle after shaken for 30 minutes.

For the evaluation of set retaining properties, the following criteria was used:

Criteria of Evaluation

A: 80% or more

B: From 60% or more to less than 80%

C: From 20% or more to less than 60%

D: Less than 20%

(2) Nonstickiness, smooth touch and gloss after finish:

Middle-length wigs were washed with a standard shampoo, and then dried with a towel. The wigs were then coated with 5 g of the setting agent while the hairs were still wet. Thereafter, these wigs were dried and set by ten female expert panels using a dryer and a brush whereby the finished wigs were organoleptically rated in accordance with the following criterion.
(Nonstickiness)

3: No stickiness

2: Little stickiness

1: Slight stickiness felt

0: Very sticky (Smooth touch)

3: Very smooth

2: Smooth

1: Not very smooth

0: Not smooth (Gloss)

3: Very glossy

2: Glossy

1: Not very glossy

0: Not glossy

The scores thus rated were averaged and evaluated in accordance with the following criterion:

A: average of 2.5 or more

B: average of 1.5 or more to less than 2.5

C: average of 0.5 or more to less than 1.5

D: average of less than 0.5

TABLE 1

| Component (% by weight) | Product of the Invention 1 | Comparative Product 1 | 2 | 3 | 4 | 5 | 6 | 7 |
| --- | --- | --- | --- | --- | --- | --- | --- | --- |
| Water-dispersible polyester (Eastman AQ55, available from Eastman Chemical Product) | 5.0 | 5.0 | — | 5.0 | 5.0 | 5.0 | 5.0 | 5.0 |
| Polyvinyl pyrrolidone | — | — | 5.0 | — | — | — | — | — |
| Polyether-modified silicone*[1] | 1.0 | — | 1.0 | 1.0 | 1.0 | 1.0 | 1.0 | 1.0 |
| Polyoxyethylene (13) cetyl ether | 0.8 | 0.8 | 0.8 | 0.8 | 0.8 | 0.8 | 0.8 | 0.8 |
| Propylene glycol | 3.0 | 3.0 | 3.0 | 3.0 | 3.0 | 3.0 | 3.0 | 3.0 |
| Isoparaffin ($C_{16}$) | 2.5 | — | — | — | — | — | — | — |
| Isopropyl myristate | — | — | — | 2.5 | — | — | — | — |
| Oleic acid | — | — | — | — | 2.5 | — | — | — |
| Oleyl alcohol | — | — | — | — | — | 2.5 | — | — |
| Cetyl alcohol | — | — | — | — | — | — | 1.0 | — |
| Hydrocarbon oil*[2] | — | — | — | — | — | — | — | 2.5 |
| Ethanol | 2.0 | 2.0 | 2.0 | 2.0 | 2.0 | 2.0 | 2.0 | 2.0 |
| Perfume | 0.05 | 0.05 | 0.05 | 0.05 | 0.05 | 0.05 | 0.05 | 0.05 |
| Purified water | balance | balance | balance | balance | balance | balance | balance | balance |

TABLE 1-continued

| Component (% by weight) | Product of the Invention 1 | Comparative Product | | | | | | |
|---|---|---|---|---|---|---|---|---|
| | | 1 | 2 | 3 | 4 | 5 | 6 | 7 |
| Liquefied petroleum gas | 10.0 | 10.0 | 10.0 | 10.0 | 10.0 | 10.0 | 10.0 | 10.0 |
| Set retaining properties | A | C | D | C | C | C | B | C |
| Nonstickiness | A | C | C | B | C | C | B | B |
| Smooth touch | A | D | C | C | C | C | C | B |
| Gloss | A | B | D | B | B | B | C | B |

*[1]Compound represented by formula (1) wherein a is from 50 to 100, b is from 1 to 5, c is 3, d is from 7 to 15, e is 0, and $R^1$ is hydrogen atom
*[2]Average carbon number: 72.

EXAMPLE 2

A foamable hair setting agent having the formulation set forth in Table 2 was prepared in an ordinary method.

The setting agent thus obtained was then evaluated for its set retaining properties and nonstickiness, smooth touch and gloss after finish in the same manner as in Example 1. The results are set forth in Table 2.

TABLE 1

| Component (% by weight) | Product of the Invention | | | | | |
|---|---|---|---|---|---|---|
| | 2 | 3 | 4 | 5 | 6 | 7 |
| Water-dispersible polyester (Eastman AQ58, available from Eastman Chemical Product) | 5.0 | 5.0 | 5.0 | 5.0 | 5.0 | 5.0 |
| Dimethyl polysiloxane (1,000 cst)*[1] | 1.0 | — | — | — | — | — |
| Dimethyl polysiloxane (100,000 cst)*[2] | — | 1.0 | — | — | — | — |
| Amino-modified silicone*[3] | — | — | 1.0 | — | — | — |
| Alkyl-modified silicone*[4] | — | — | — | 1.0 | — | — |
| Stearoxy-modified silicone*[5] | — | — | — | — | 1.0 | — |
| Silicone resin*[6] | — | — | — | — | — | 0.5 |
| Polyoxyethylene(13) cetyl ether | 0.3 | 0.3 | 0.3 | 0.3 | 0.3 | 0.3 |
| Glycerin | 5.0 | 5.0 | 5.0 | 5.0 | 5.0 | 5.0 |
| Isoparaffin ($C_{12-16}$) | 1.0 | 1.0 | 5.0 | 5.0 | 5.0 | 5.0 |
| Methyl parabene | 0.1 | 0.1 | 0.1 | 0.1 | 0.1 | 0.1 |
| Purified water | balance | balance | balance | balance | balance | balance |
| Liquefied petroleum gas | 10.0 | 10.0 | 10.0 | 10.0 | 10.0 | 10.0 |
| Set retaining properties | A | A | A | A | A | A |
| Nonstickiness | B | A | A | A | A | A |
| Smooth touch | B | B | A | A | A | B |
| Gloss | A | A | A | A | A | A |

*[1]Silicone KF96 (available from Shin-Etsu Chemical Co., Ltd.)
*[2]Silicone KF96H (available from Shin-Etsu Chemical Co., Ltd.)
*[3]Toray 8702C (available from Toray Industries, Inc.)
*[4]Compound represented by formula (6) wherein $R^3 = C_{16-18}$, i = 100 to 150, and j = 100 to 150
*[5]Compound represented by formula (7) wherein $R^4 = C_{16-18}$, K = 10 to 20, and l = 5 to 10
*[6]Compound represented by formula (11) wherein $R^7 =$ methyl group (u/v = about 0.8; molecular weight: about 3,000)

EXAMPLE 3

A gel hair setting agent having the formulations shown below was prepared by an ordinary method.

The setting agent thus obtained exhibited excellent set retaining properties and provided hairs with a nonsticky smooth finish touch and a natural gloss.

| Component | Component (% by weight) |
|---|---|
| Water-dispersible polyester (Eastman AQ38, available from Eastman Chemical Product) | 5.0 |
| Isoparaffin ($C_{16}$) | 0.5 |
| Hydroxyethyl cellulose | 1.2 |
| Carboxyvinyl polymer (Carbopole 940, available from Goodrich Inc.) | 0.6 |
| Bunte salt-modified silicone* | 0.8 |
| Glycerin | 4.5 |
| Triethanolamine | to make pH 7.5 |
| Methyl parabene | 0.1 |
| Perfume | 0.1 |
| Purified water | Balance |
| Total | 100.0 |

*Compound represented by formula (10) wherein r = 3, s = 15 to 20, and Y = Na

EXAMPLE 4

A sprayable hair setting agent having the formulation shown below was prepared in an ordinary method.

The setting agent thus obtained exhibited excellent set retaining properties and provided hairs with a nonsticky smooth finish touch and a natural gloss.

| Component | Component (% by weight) |
|---|---|
| Isoparaffin (about $C_{20}$) | 1.0 |
| Water-dispersible polyester (Eastman AQ55, available from Eastman Chemical Product) | 1.5 |
| Polyether-modified silicone* | 0.7 |
| Glycerin | 2.0 |
| Polyoxyethylene(10) monolaurate | 0.5 |
| Perfume | 0.05 |
| Ethanol | 10.0 |
| Purified water | Balance |
| Dimethyl ether | 25.0 |
| LPG | 5.0 |
| Total | 100.0 |

*Silwet 1-7002, available from Nihon Unicar Co., Ltd.

EXAMPLE 5

An aerosol sprayable hair setting agent having the formulation shown below was prepared in an ordinary method.

The setting agent thus obtained exhibited excellent set retaining properties and provided hairs with a nonsticky smooth finish touch and a natural gloss.

| Component | Component (% by weight) |
| --- | --- |
| Isoparaffin ($C_{12}$) | 0.5 |
| Water-dispersible polyester (Eastman AQ55, available from Eastman Chemical Product) | 1.0 |
| Polyether-modified silicone* | 1.0 |
| Propylene glycol | 2.2 |
| Polyoxyethylene (13) cetyl ether | 0.5 |
| Polyoxyethylene (2) lauryl ether | 0.3 |
| Perfume | 0.02 |
| Ethanol | 10.0 |
| Methyl parabene | 0.08 |
| Nitrogen gas | 0.9 |
| Purified water | Balance |
| Total | 100.0 |

*Silicone XF352A, available from Shin-Etsu Chemical Co., Ltd.

While the invention has been described in detail and with reference to specific embodiments thereof, it will be apparent to one skilled in the art that various changes and modifications can be made therein without departing from the spirit and scope thereof.

What is claimed is:

1. A hair setting agent composition comprising:

(A) 0.01 to 10% by weight of a water-dispersible polyester resin having a —$SO_3M$ group in which M is a hydrogen or metal ion in an amount sufficient to render the polyester dispersible in water;

(B) 0.01 to 10% by weight of at least one silicone derivative selected from the group consisting of a polyether-modified silicone, a dimethyl polysiloxane, a methylphenyl polysiloxane, a diphenyl polysiloxne, a $C_{10-50}$ alkyl-modified silicone, an alkoxy-modified silicone, an amino-modified silicone, a Bunte salt-modified silicone and a silicone resin; and (C) 0.1 to 40% by weight of a $C_{12-20}$ hydrocarbon oil.

2. The hair setting agent composition of claim 1, wherein said water-dispersible polyester resin is a polyester resin obtained by the condensation of at least one dicarboxylic acid, at least one diol and at least one bifunctional sulfo monomer comprising an aromatic nucleus having two functional groups selected from carboxylic and hydroxy groups and at least one sulfonic group.

3. The hair setting agent composition of claim 1, wherein said water-dispersible polyester resin is one obtained by the condensation of diethylene glycol, cyclohexanedimethanol, isophthalic acid and sulfoisophthalic acid.

4. The hair setting agent composition of claim 1, wherein said silicone derivative is said polyether-modified silicone, said dimethyl polysiloxane, said methylphenyl polysiloxane or said diphenyl polysiloxane.

5. The hair setting agent composition of claim 1, wherein a propellent is further present in an amount of from 3 to 50% by weight.

6. A hair setting method comprising coating or spraying on hair a composition comprising:

(A) 0.01 to 10% by weight of a water-dispersible polyester resin having a —$SO_3M$ group in which M is a hydrogen or metal ion in an amount sufficient to render the polyester dispersible in water;

(B) 0.01 to 10% by weight of at least one silicone derivative selected from the group consisting of a polyether-modified silicone, a dimethyl polysiloxane, a methylphenyl polysiloxane, a diphenyl polysiloxne, a $C_{10-50}$ alkyl-modified silicone, an alkoxy-modified silicone, an amino-modified silicone, a Bunte salt-modified silicone and a silicone resin; and (C) 0.1 to 40% by weight of a $C_{12-20}$ hydrocarbon oil.

* * * * *